US005679643A

United States Patent [19]

Kauvar et al.

[11] Patent Number: 5,679,643
[45] Date of Patent: Oct. 21, 1997

[54] GLUTATHIONE ANALOGS AND PARALOG PANELS COMPRISING GLUTATHIONE MIMICS

[75] Inventors: Lawrence M. Kauvar, San Francisco; Matthew H. Lyttle, Point Reyes Station, both of Calif.

[73] Assignee: Terrapin Technologies, Inc., San Francisco, Calif.

[21] Appl. No.: 253,433

[22] Filed: May 31, 1994

Related U.S. Application Data

[63] Continuation of Ser. No. 863,564, Apr. 3, 1992, abandoned, which is a continuation-in-part of Ser. No. 693,245, Apr. 29, 1991, abandoned, which is a continuation-in-part of Ser. No. 447,009, Dec. 6, 1989, Pat. No. 5,300,425, which is a continuation-in-part of Ser. No. 225,906, Oct. 11, 1988, Pat. No. 5,217,869, which is a continuation-in-part of Ser. No. 108,130, Oct. 13, 1987, abandoned, said Ser. No. 863,564, is a continuation-in-part of Ser. No. 678,849, Apr. 2, 1991, Pat. No. 5,338,659, and Ser. No. 607,895, Nov. 1, 1990, abandoned, which is a continuation-in-part of Ser. No. 429,721, Oct. 31, 1989, Pat. No. 5,113,866, which is a continuation-in-part of Ser. No. 355,042, May 16, 1989, Pat. No. 4,963,263.

[51] Int. Cl.$^6$ .............................. A61K 38/00; C07K 5/00
[52] U.S. Cl. ................................. 514/18; 530/330
[58] Field of Search ......................... 530/330; 514/18

[56] References Cited

U.S. PATENT DOCUMENTS

| 4,963,263 | 10/1990 | Kauvar | 210/635 |
| 5,133,866 | 7/1992 | Kauvar | 210/635 |

FOREIGN PATENT DOCUMENTS

| 0 480 061 | 4/1992 | European Pat. Off. |
| 1 317 275 | 5/1973 | United Kingdom . |
| WO 92/00320 | 1/1992 | WIPO . |
| WO 92/19767 | 11/1992 | WIPO . |
| WO95/08563 | 3/1995 | WIPO . |
| WO95/09866 | 4/1995 | WIPO . |

OTHER PUBLICATIONS

Ciaccio P.J. et al. "Modulation of Detoxification Gene Expression in Human Colon HT29 Cells by Glutathione–S–Transferase Inhibitors" *Molecular Pharmacology* 48:639–647 (1995).
Annual Meeting of the Canadian Society for Clinical Investigation and the Royal College of Physicians and Surgeons of Canda, Montreal, Quebec, Canada, Sep. 13–17, 1995, "Clinical and Investigative Medicine, " vol. 18 (4 Suppl.) (1995), Cournoyer D. et al.
Morgan A. S. et al. "Isozyme-specific Glutathione S–Transferase Inhibitors Potentiate Drug Sensitivity in Cultured Human Tumor Cell Lines," *Cancer Chemother. Pharmacol.* 37:363–370 (1996).
T. Kasai et al., *Phytochemistry* "γ-Glutamyl Peptides of Vigna Radiata Seeds" vol. 25, pp. 679–682.
R. Camble, et al., *J. Chem. Soc.* "The Use of S–Benzylthiomethyl–L–cysteine in Peptide Synthesis: Synthesis of Glutathione and Homoglutathione" (1968) 7/1515:1219–1224.

Mozer et al., "Purification and Characterization of Corn Glutathione S–Transferase", Biochemistry 22: 1068–1072 (1983).
Sheh, L., Synthesis of cyclic peptide homologs of glutathione as potential antitumor agents, Int. J. Peptide Protein Res. (1990) 35:55–62.
Webster's II New Riverside University Dictionary, The New Riverside Publishing Company, 1988, p. 849.
Principato et al. (1989) 41: 175–180 Enzyme.

*Primary Examiner*—Robert J. Hill, Jr.
*Assistant Examiner*—Bennett Celsa
*Attorney, Agent, or Firm*—Morrison & Foerster LLP

[57] ABSTRACT

Compounds of the formula:

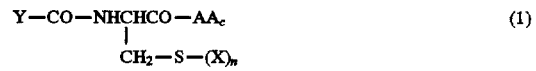

or a salt thereof, wherein n is 1 or 2;
wherein when n is 1, X is a mono- or disubstituted or unsubstituted $C_{1-20}$ hydrocarbon radical wherein any substitution is selected from the group consisting of halo, OR, and SR, wherein R is H or $C_{1-4}$ alkyl;

and wherein, when n is 2, one X is defined as for n=1 and the other X is lower $C_{1-4}$ alkyl;

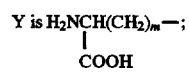

wherein m is 1 or 2;
$AA_C$ is an amino acid coupled through a peptide bond to the remainder of the compound of Formula (1) selected from the group consisting of glycine, valine, alanine, 4-aminobutyric acid, aspartic acid, phenylglycine, histidine, tryptophan, tyrosine, and phenylalanine, wherein the phenyl group of phenylalanine or phenylglycine may optionally contain a single substitution selected from the group consisting of halo, OR, and SR, wherein R is H or $C_{1-4}$ alkyl;

with the proviso that if Y is

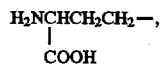

$AA_C$ is not Gly;
and if Y is

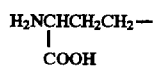

and X is benzyl, $AA_C$ cannot be Val are useful as affinity ligands and as diagnostic reagents. These compounds and analogous tripeptide glutathione analogs can be used as members of panels to obtain specific characteristic profiles for various glutathione-S-transferases.

18 Claims, No Drawings

GLUTATHIONE ANALOGS AND PARALOG PANELS COMPRISING GLUTATHIONE MIMICS

This application is a continuation of application Ser. No. 07/863,564, filed 3 Apr. 1992 (abandoned), which is a continuation-in-part of U.S. Ser. No. 07/693,245, filed 29 Apr. 1991 (abandoned) which is a continuation-in-part of U.S. Ser. No. 447,009 filed 6 Dec. 1989 now U.S. Pat. No. 5,300,425 which is a continuation-in-part of U.S. Ser. No. 255,906, filed 11 Oct. 1988 now U.S. Pat. No. 5,217,869, which, in turn, is a continuation-in-part of U.S. Ser. No. 108,130, filed 13 Oct. 1987 now abandoned. Ser. No. 07/863,564 is also a continuation-in-part of U.S. Ser. No. 607,895, filed 1 Nov. 1990, now abandoned, which is a continuation-in-part of U.S. Ser. No. 429,721, filed 31 Oct. 1989 now U.S. Pat. No. 5,133,866, which is a continuation-in-part of U.S. Ser. No. 355,042, filed 16 May 1989, now U.S. Pat. No. 4,963,263. Ser. No. 07/863,564 is also a continuation-in-part of U.S. Ser. No. 678,849, filed 2 Apr. 1991 now U.S. Pat. No. 5,338,659.

TECHNICAL FIELD

The invention relates to tripeptide compounds which are novel analogs of glutathione. The invention also concerns panels of tripeptides that are glutathione analogs which have diverse properties and are useful for characterizing glutathione transferases (GSTs) and as solution phase inhibitors of GST.

BACKGROUND ART

Glutathione (GSH), in its reduced form, is a tripeptide of the formula: γ-Glu-Cys-Gly. Reduced glutathione has a central role in maintaining the redox condition in cells and is also an essential substrate for glutathione S-transferase (GST) which facilitates the detoxification of foreign substances by a number of mechanisms, including catalysis of the coupling of an electrophilic portion of a toxin, for instance, to glutathione, rendering the toxin more susceptible to clearance. A second mechanism, which also involves glutathione as substrate, resides in the reduction of peroxides with the concomitant oxidation of glutathione.

Adang, A. E. P., et al., *Biochem J* (1990) 269:47–54, described tripeptide analogs of GSH which interact with various GST isoenzymes at different concentrations. These analogs are modified forms of GSH in which at least one of the glycine, cysteine, or gamma-glutamine residues is replaced by an alternate amino acid residue.

Additional modified forms have been disclosed, for example, by Principato, G. B., et al., *Enzyme* (1989) 41:175–180, who studied the effect of a tripeptide GSH analog on glyoxalase II enzyme of rat liver. The tripeptide used by this group was of the formula γ-Glu-p-chlorophenylcarbonylmethyl-Cys-Gly-Cys-Ser. Morris, D., in *Biochem J* (1960) 76:349–353, described the synthesis of γ-Glu-benzyl-Cys-Val. A large number of GSH tripeptide analogs containing a substitution for only one of the three GSH amino acids have been reported and are commercially available.

The invention described hereinbelow concerns novel glutathione tripeptide analogs which are useful as affinity ligands on chromatographic supports and as members of panels which are used to characterize the various isoenzymes of glutathione-S-transferase. Glutathione-S-transferases (GSTs) are present in the form of a number of isoenzymes which differ in specific binding abilities, in substrate and inhibitor specificities and in tissue distribution. Particular complements of GST isoenzymes, with their accompanying differences in properties, thus are characteristic of specific tissues or cell types, such as tumor tissues. As GST is central to the overall metabolism of the tissue or cell as it relates to its defense against toxic substances, the character of the complement of the GST for the cell or tissue is important in designing strategies either for the destruction of the cell or tissue, as would be desirable for tumor cells, or for enhancement of its metabolic function, as would be the case for normal tissue.

The various GST isoenzymes are dimeric proteins formed by binary combinations of monomers encoded by at least fifteen known genes in four gene families resulting in the theoretical possibility of several dozen different dimers, even allowing for preferential dimerization of monomers from the same gene family. In addition to the variability that arises from these combinatorial possibilities, the GST isoenzyme subunits are polymorphic in the human population and have been considered to subject to additional variation due to gene conversion events among the tandemly repeated members of the family. Posttranslational modifications add further to this variability. As each cell or tissue may contain one or several of these theoretically possible enzymes, determination of the GST complement is of great importance.

The present invention, by providing novel glutathione analogs which are useful as sorbents and as solution phase inhibitors, as well as panels that include them, offers an improved method to characterize individual GST enzymes or sets thereof.

DISCLOSURE OF THE INVENTION

The invention is directed to reagents useful in characterizing glutathione S-transferase isoenzymes, and determining the GST complements of cells and tissues. The invention compounds are systematically modified forms of reduced glutathione and panels comprising such analogs having diverse properties with respect to the targeted enzymes. The invention compounds are also useful as chromatographic affinity ligands, binding reagents, and enzyme inhibitors.

Thus, in one aspect, the invention is directed to compounds of the formula:

or the monoalkyl (1–6 C) amides, alkyl (1–6 C) esters, salts or the cycloamido forms thereof;

wherein n is 1 or 2;

wherein when n is 1, X is a mono- or disubstituted or unsubstituted hydrocarbyl (1–20 C) moiety optionally containing 1 or 2 nonadjacent heteroatoms (O, S or N), and wherein said substitution is selected from the group consisting of halo, OR, and SR, wherein R is H or lower alkyl (1–4 C); and wherein, when n is 2, one X is as above defined and the other X is lower alkyl (1–4 C);

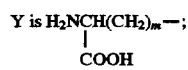

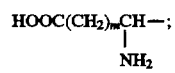

-continued

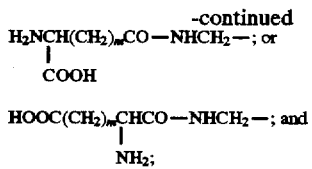

AA$_C$ is an amino acid coupled through a peptide bond to the remainder of the compound of Formula (1);
with the proviso that if Y is

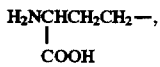

AA$_C$ is not Gly;
and if Y is

and X is benzyl, AA$_C$ cannot be Val.

In another aspect, the invention is directed to panels of diverse tripeptide glutathione analogs wherein said analogs are of Formula (1) above, wherein Y, AA$_C$ and X are as above defined, but X may also be H. Panels containing at least five such tripeptides of diverse properties are useful as substrates for determination of spectrum of characteristics (SC) profiles of standards, which, in turn are useful for comparison with samples to determine GST complement.

MODES OF CARRYING OUT THE INVENTION

The invention is directed to compounds that are novel and useful individually as chromatographic ligands and as GST inhibitors, as well as to panels of related compounds which have diverse properties and which are useful in determining profiles, for example, of GST enzymes, and in determining GST complement in unknown samples.

Use as Chromatographic Ligands

The invention compounds are useful individually as diagnostic chromatographic supports and as inhibitors of enzymes which utilize glutathione as substrate. For use as affinity ligands on chromatographic support, the invention compounds are coupled to a suitable solid matrix, such as Sepharose, polyacrylamide, silica, and the like using standard coupling techniques. The noncyclic forms of the compounds of the invention contain at least amino and carboxyl functional groups which can be derivatized to suitable linkers or directly to supports. Depending on the nature of the solid support, the coupling of the affinity ligand may employ direct covalent coupling or may require the use of homo- or heterobifunctional linkers such as those available from Pierce Chemical Company (Rockford, Ill.). It may also be desirable to distance the affinity ligand from the surface of the support in order to render it more accessible. Such distancing can be accomplished using spacer arms, as is generally understood. Further, the support may be treated with an inert material, such as, for example, human serum albumin, so as to minimize unwanted interactions, especially if the support is to be used for the chromatography of biological samples.

The chromatographic supports derivatized to the compounds of the invention may then be used for preparative separation of materials for which the compounds have an affinity, such as enzymes utilizing glutathione as substrate, antibodies which react with glutathione, or other moieties which bind with moderate affinity to the compounds of the invention. Chromatographic supports coupled to the compounds of the invention may also be used in diagnosis to determine the presence, absence, quantity or nature of materials in biological or other samples suspected to contain materials having similarity in structure to glutathione.

The suitable compound of the invention useful in such separations or analyses may be evident from the nature of the analyte or material whose preparation is desired, or may readily be determined by preparing a diverse panel of the compounds of the invention and screening the panel for the most effective affinity ligand.

Use of the Invention Compounds as Inhibitors

In addition to their use as affinity ligands in chromatography, the compounds of the invention are also useful as solution-phase inhibitors of enzymes, such as glutathione-S-transferases, which utilize glutathione as substrates. Such inhibition may be desirable both in analytical and therapeutic contexts.

Use of the Invention Panels

The panels are useful in determining the differing complements of the glutathione-S-transferase (GST) isoenzymes as they occur in normal (as compared to unwanted) cells or tissues. By "GST complement" is meant the pattern of levels of GST isoenzymes that is present in such cells or tissues or which is genetically programmed in such a manner that induction or repression of expression levels of such GSTs is manipulable. As explained in the Background section above, GSTs are homo- or heterodimers formed from subunits, of which at least seven are well known. In addition, although these isoenzymes have been classified broadly, individual members within each class may differ from individual to individual due to genetic variation. The properties of the various isoenzymes differ with respect to a series of measurable parameters including substrate specificity, susceptibility to inhibition, binding to specific reagents, and inducibility of expression. The use of the invention panels is further described in detail below.

The Compounds of the Invention

The novel compounds of the invention are of Formula 1, wherein at least one X is a mono- or disubstituted or unsubstituted hydrocarbon radical (1–20 C) moiety optionally containing one or two nonadjacent heteroatoms (O, S or N).

As used herein, "hydrocarbon radical" refers to a straight or branched chain or cyclic, saturated or unsaturated, aliphatic or aromatic hydrocarbon radical residue containing 1–20 C. In addition to the 1–20 C, where structurally realistic, the hydrocarbon radical may also contain one or two nonadjacent heteroatoms which are O, S or N. Thus, the hydrocarbon radical group so modified may be an ether, a diether, a thioether or a dithioether, or a secondary or tertiary amine or diamine. Representative of such substituents include methyl, ethyl, propyl, isopropyl, butyl, tertiary butyl, hexyl, octyl, nonyl, 2,3-dimethyloctyl, dodecyl, 9,9-dimethylundecyl, allyl, 2-butenyl, isobutenyl, cyclohexyl, cyclopentyl, cycloheptyl, phenyl, benzyl, 4-methylbenzyl, triphenylmethyl (trityl or trt), methoxyethyl, ethylthioethyl, diethylaminopropyl, and the like.

In addition, the hydrocarbon or hydrocarbon radical containing one or two heteroatoms may optionally be substituted by one or two substituents selected from halo, i.e., fluoro, chloro, bromo or iodo, or hydroxy or sulfhydryl, and/or alkyloxy or alkylthio, such as methylthio, butylthio, propoxy or ethoxy.

AA_C may be any gene-encoded amino acid except that when Y is

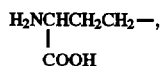

AA_C cannot be glycine; and when Y is

and X is benzyl, AA_C must be other than valine. In addition, AA_C may also be an amino acid residue which is not encoded by the gene, such as hydroxyproline (HP), 4-aminobutyric acid (4-Bu), β-alanine (bA), phenylglycine (PG), and the like. AA_C is thus bound to the compound of Formula 1 through a peptide bond.

The compounds of the invention may also be prepared in the forms of their alkyl esters or alkyl amides, or as their salts, or in the amidocyclic forms.

Alkyl esters of the free carboxyls are esters of the straight- and branched-chain alkyl alcohols (1–6 C) such as methanol, ethanol, isopropanol, t-butanol, n-hexanol and the like. Suitable alkyl (1–6 C) amides are those of primary straight- or branched-chain alkyl amines, such as methylamine, ethylamine, n-propylamine, isopentylamine, and isohexylamine. The esters and amides are prepared using conventional techniques, with suitable protection of any alcohol or amino functional groups in the substrate compound of Formula 1.

The salts of the compounds of the invention may be formed of inorganic bases such as sodium or potassium hydroxide or of organic bases such as caffeine or piperidine to form the basic salts of the free carboxyl groups or may be formed from organic or inorganic acids to obtain the acid addition salts off free amino groups. Thus, the salts may be of inorganic bases such as sodium hydroxide, calcium hydroxide, ammonium hydroxide, magnesium hydroxide, and the like, or of organic bases such as trimethylamine, pyridine, pyrimidine, lysine, caffeine, and the like. The acid addition salts may be formed from inorganic acids such as hydrochloric acid, hydrobromic acid, sulfuric acid, phosphoric acid, and the like, or from organic acids such as acetic acid, propionic acid, glycolic acid, pyruvic acid, oxalic acid, malic acid, tartaric acid, citric acid, benzoic acid, cinnamic acid, mandelic acid, salicylic acid, and the like.

The salts of the compounds of Formula 1 are formed in standard protocols by treating with the appropriate base or acid at a temperature of from about 0° C. to about 100° C., preferably at room temperature either in water alone or in combination with an inert water-miscible organic solvent such as methanol, ethanol or dioxane.

In addition to the esters, amides, and salts of the compounds of formula 1, these compounds may be prepared in cyclic form by bridging free amino and free carboxyl groups contained in the substrate compound. Formation of the cyclic compounds is conducted conventionally by treatment with a dehydrating agent such dicyclohexyl carbodiimide by means known in the art per se.

The compounds of the invention can be characterized by designating the identities of Y, n, X and AA_C. In order to designate Y, the carbonyl group shown adjacent the Y substituent in Formula 1 is conveniently included in the designation; if this is the case, the various embodiments of "Y-CO" include γ-Glu, β-Asp, Glu, Asp, γ-Glu-Gly, β-Asp-Gly, Glu-Gly, and Asp-Gly, which in the 1-letter amino acid codes can be symbolized as gE, bD, E, D, gE-G, bD-G, E-G, and D-G, respectively.

The various substituents designated by X can be noted by standard abbreviations, and their inclusion in the tripeptide analogs of the compounds of the invention symbolized by C(X) when n=1 or C(X)(X) when n=2. In those compounds of formula 1 wherein n equals 2, the sulfur of the cysteine residue will have a positive charge and exist as a sulfonium ion.

The notation for AA_C may also be in the standard one-letter amino acid abbreviation code or other suitable abbreviation for non-gene encoded amino acids.

Thus, using this notation, suitable compounds of the invention include:

gE-C(Bz)(Me)-G,
bD-C(Trt)-A,
E-C(Pr)(Me)-V,
(cyclo)bD-C(Hx)-PG,
E-G-C(Bz)(Et)-4ABu, (SEQ ID NO:1)
D-G-C(Hx)-F, (SEQ ID NO:2)
gE-C(Hx)(Me)-N,
(cyclo)gE-C(Trt)-N, and the like.

Panels

The panels of the invention are constructed of at least five diverse tripeptide analogs of glutathione of Formula 1, wherein X, AA_C and Y are as defined above but wherein X can also be H. The panels are most useful when maximally diverse in character. This diversity can be supplied by varying the natures of Y, AA_C and X. In general, by using X substituents, for example, of varying hydrophobicity, a range of such hydrophobicity characteristics can be obtained. X is also a convenient substituent for variation of the Hammett Constants (sigma/meta and sigma/para) diversity of the resulting compounds. The diversity resulting from variation of AA_C is somewhat less focused; that provided by variations in Y is limited by the limitations on that structure.

The Hammett Constants refer to the values analogous to those obtained showing the electronic influence of substituents on the ionization constant of benzoic acid. As a result of this early work, numerical values have been assigned to a large array of different substituents. Tables of such values for various substituents are given, for example, by Ritchie, C. D. et al., *Prog Phys Org Chem* (1964) 2:323.

The construction of a series of the analogs of the invention can be made which systematically varies the value of this parameter by, for example, utilizing as the embodiment of X, a benzyl group which is further substituted with an additional substituent at the para position, such as nitro, chloro, methoxy, or methyl.

The steric characteristics and the resulting properties of the compounds of Formula 1 which are members of the panel can also be controlled by cyclization of one or more members of the panel.

For example, a two-dimensional matrix of the glutathione analog tripeptides of the invention forming a suitable two-dimensional panel can be constructed by varying the AA_C component from a small hydrophobic residue to a large hydrophobic residue to a positively charged residue to a neutral residue and finally to a negatively charged residue, thus influencing, in the latter three analogs, the inductive electronic effect. Similarly, the X substituents can be varied in the second dimension over the same range from small hydrophobic to large hydrophobic to positively charged to neutral to negative. The resulting matrix provides a suitable panel for use in, for example, determining suitable compounds to use as adsorbents.

Use of the Invention Panels to Determine GST Profiles—Background

Perhaps the most easily understood approach to determining the GST isoenzyme complement of an unknown tissue sample presumes a reference set of all GST isoenzymes which have reactivity profiles that have been or can be determined. Thus, assuming a high enough resolution separation, for example, using any separation technique, analogous, for example, to high resolution chromatographic focusing, an elution pattern is referenced to a series of known enzymes. Other methods for separating and characterizing the known isoenzymes could include the use of antibodies that have been prepared to specific isoenzymes, such as those established for several GST human isotypes and used to assess GST content of these isotypes in candidate tissues (Howie, A. F., et al., *Carcinogenesis* (1990) 11:451–458; Beckett, G. J. *Clinica Chimica Acta* (1984) 141:267–273). Gel electrophoresis separations can also be used. The location of the GST bands following electrophoresis under nondenaturing conditions can be determined, for examples, by the method of Ricci, G., et al., *Anal Biochem* (1984) 143:226–230. The location of various isoenzymes resulting from chromatographic separations can be detected using substrates common to all isoenzymes, such as 1-chloro-2,4-dinitrobenzene (CDNB). Indeed, the distribution of activity as assayed by CDNB in various tissues has been conducted by Pickett, C. B., and Lu, A. Y. H., *Ann Rev Biochem* (1989) 58:743–764.

The use of these direct separation methods to obtain a pattern of GST isoenzyme distributions in cells and tissues of interest can be used to obtain a GST complement for such cells and tissues that may be useful in the design of therapy, provided that each of these isoenzymes has a reactivity profile which has been determined previously following separation techniques permitting isolation of the individual isoenzyme with retention of activity. Such a reactivity profile would take account of the substances which are effective substrates, substances which are effective inhibitors, and substrates which are effective inducers or activators of GST activity. Once the GST isoenzyme is identified and quantitated by virtue of its position in the elution pattern or electrophoretic gel, for example, reference is made to the reactivity profile of the known and previously isolated isoenzyme in order to predict or design treatment protocols.

This method, while readily comprehensible, is not practical due to the large number of GST isoenzymes that are potential candidates for inclusion in the complement and due to the mutability of the repertoire of GST isoenzymes per se. Thus, a polymorphism in the population of available GST isoenzymes is likely to result in a protein with unaltered mobility, for example, in the elution pattern, but with altered substrate specificity or inhibition pattern, or vice versa. In either case, the results of the matching of the position in the elution pattern to the set of reference characteristics would give misleading results.

A somewhat improved result can be obtained by utilizing multiple separation techniques, it being less likely that mobility would be unaffected in multiple separation systems as compared to one. Such a system is generically illustrated in FIG. 1 which indicates that on sorbent P1 four isoenzyme peaks are obtained in the elution pattern; five are obtained in P2. The substrate specificity patterns (for substrates A, B and C) indicate that peak 1.5 is substantially the same in substrate profile as peaks 2.1 and 2.2 separated on sorbent P2; the isoenzyme that elutes at position 1.2 in sorbent P1, according to substrate specificity pattern, elutes at position 2.4 in sorbent P2. Correlations are also shown between peaks 1.12 and 2.14 and peaks 1.14 and 2.15, again using substrate specificity as a criterion.

One would therefore assume that a tissue sample which provided a peak at 1.2 in sorbent P1 and at 2.4 in sorbent P2 would be highly likely to have a reactivity profile wherein A was the only active substrate, and at a relatively low level.

The technique illustrated in FIG. 1 can be applied using, as affinity-based sorbents, the novel glutathione tripeptide analogs of the invention or one such novel tripeptide in combination with an additional analog or panels of analogous glutathione analogs with diverse properties. It is believed that to perform effective characterization, a panel of at least two, and preferably three, such analogs should be used. The members of the panel should have properties which are sufficiently diverse to assure discrimination among the various GST isoenzymes in the complement.

If the separation technique preserves enzymatic activity, the reactivities of each enzyme against potential drugs can be directly determined. Nondenaturing separations in the art, however, suffer from either a lack of resolution or from hypersensitivity to structural changes, making peak identification too problematic for effective guidance of therapy. Ion exchange chromatography, for example, can be used as a step to purify individual GST isoenzymes, but has inadequate or inappropriate resolution as an analytical tool. IEF, another technique available in the art, is prone to generation of numerous extraneous peaks due to in vivo or in vitro posttranslational modification of the protein, and there is no necessary linkage between such structural changes and functional variation.

Thus, determination of the activity profile of the GST complement in cells or tissues by separating the individual isoenzymes using prior art methods and determining an activity profile for each of them against all possible chemotherapeutic drugs would be laborious, but is enhanced by the availability of the novel GSH-analog tripeptides of the invention. The compounds of the invention permit separation without denaturation of the GST enzymes.

A more efficient approach takes advantage of profiles of GST isoenzyme complements which simultaneously measure specific binding activity and reactivity characteristics. These profiles, designated survey of characteristics profiles, or "SC" profiles, permit the determination of a reference set of SC profiles which include information on substrate specificity, induction in response to specific inducers, and the like, as well as additional binding or electrophoretic mobility characteristics. By applying computational methods to comparison of these profiles, the requisite information for the design of therapeutic modulators and accompanying protocols and for prediction of success or failure of proposed protocols can be obtained for significantly larger numbers of specimens than by prior art methods, as is needed to provide an adequate guide for therapy. Among the parameters that can be used for obtention of an SC profile is the ability to bind to members of the panels of tripeptide GSH analogs of the invention, or the effect of such panel members on activity.

In this approach to determining the GST complement of unknown samples of cells and tissues, advantage is taken of pattern recognition techniques. In connection with this approach, what is here termed an SC profile is determined generally with respect to a panel of reagents which react specifically and differentially with the various GST isoenzymes. This is analogous to the determination of profiles obtained by cross-reaction immunoassay, and refers to any pattern of reactivity of a candidate GST isoenzyme or mixture of isoenzymes with a panel of reagents. Thus, the SC profile may be determined with respect to turnover rates for various substrates; effective levels of inhibitor concentration for various inhibitors; levels of inducers required to induce the expression of the gene for the GST isoenzyme in the context of a particular host cell; mobility in electrophoresis in the presence or absence of inhibitors or substrates; elution times from paralog or other affinity columns or, indeed, the classical pattern of binding with a panel of antibodies. The SC profiles obtained for individual GST isoenzymes or mixtures of isoenzymes at various concentration levels can be manipulated in various ways, described herein, to provide a reference set against which SC profiles of unknown samples can be compared.

In general, the SC profile will provide values for each of a panel of "information channels" wherein each information channel describes a characteristic of the GST complement or standard, such as the binding affinity for an antibody, a substrate affinity, an elution time or the like. At least some of the information channels should relate to values that vary with concentration of the GST.

Determination of the GST complement for cells or tissues is useful per se in diagnosis and characterization of samples. In addition, for use in the design of embodiments of the strategies to impair or destroy unwanted tissue, the SC profiles must provide information related to GST activity so that activity differences between normal and unwanted tissues can be determined. Thus, the SC profiles of the unwanted tissue must be readily comparable to the reference standards which, in turn, must at least in part be based on reactivity patterns that will aid in the design of therapeutic modulators and the selection of drugs or prodrugs. For this application, at least a portion of the reference profiles must be grounded in substrate turnover rate data, inhibition data, or data relating to induction of isoenzyme production level, or any other reactivity which will permit manipulation of the GST isoenzyme in situ. The panels of the invention may be used to determine such effects on activity. The combination of chromatographic separation which permits activity to be retained using the novel compounds of the invention along with preparation of SC profiles with regard to reactivity-affecting reagents for these standards is one approach to obtaining the needed data.

The SC profiles of the reference standards and of the unknown samples are determined with respect to panels of "specifically reactive reagents." These reagents may include a variety of substances, including paralogs, substrates, inhibitors, inducers, antibodies, as well as "reagents" which are actually techniques such as gel electrophoresis or affinity chromatography where the extent of reactivity is determined as electrophoretic mobility or elution time. Thus, "specifically reactive reagents" is not limited to those reagents which effect a chemical reaction, but includes any reagent or technique that permits a characteristic parameter to be obtained for the sample with respect to that reagent.

Of course, the panels of the analogs of the invention can be used as "specifically reactive reagents" either as binding agents, chromatographic supports, or as inhibitors of enzyme action in solution. The comparative ability of these compounds as members of the panel to inhibit the enzymatic reactions catalyzed by GST can be used as a characteristic SC profile, as can elution patterns from columns containing the tripeptide analogs as affinity ligands.

Determination of Reference SC Profiles

While reference standards for some purposes, as described below, can be prepared directly from normal tissue of a particular subject, it is also useful to provide a databank of SC profiles for a variety of previously isolated GST isoenzymes with characteristic reactivity patterns. By matching these reactivity patterns with those from biopsy samples of the unwanted tissue, the appropriate design for therapeutic modulators and choice of prodrugs or toxins can be made.

U.S. Pat. No. 4,963,263 and U.S. Ser. No. 429,721, for which the issue fee has been paid, the disclosures of which are incorporated herein by reference, describe panels of paralog affinity reagents that are useful in chromatographic separations of closely related substances. The panels of the invention are similarly diverse. Paralog-type panels using the GSH tripeptide analogs of the invention can be conveniently used in the preparation of affinity supports for the separation of various GST isoenzymes in purified form while, in each case, retaining the activity of the native isoenzyme. Unlike the reverse-phase HPLC or Western blot methods of the prior art, the separated isoenzymes prepared using chromatography based on affinity for the compounds of the invention behave in a manner virtually precisely similar to that of the isoenzymes as they occur in nature. For each such purified isoenzyme, then, a SC profile with respect to reactivity of substrate or other activity-affecting reagent such as those represented by the compounds of the invention can be constructed. A helpful databank of a large number of SC profiles characteristic of these purified isoenzymes can then be retained and stored in mathematically or computationally accessible form for comparison to samples obtained from the unwanted tissue.

Panels of tripeptide glutathione analogs, at least one member of which is of Formula 1, can be used as the basis for the collection of information channels which provides the SC profiles for the reference set. Conjugation of known isoenzyme specific substrates to the members of the panel or conjugation of the members of the panel directly to sorbent further increases the systematic diversification of binding properties. Profiles for standards and unknown samples can be obtained and compared using the panels of the invention in appropriate configurations, such as affinity columns.

Thus, particularly useful are panels of diverse tripeptide analogs including at least one analog of Formula 1 wherein X is a mono- or disubstituted or unsubstituted hydrocarbyl (1–20 C) moiety optionally containing 1 or 2 nonadjacent heteroatoms (O, S or N), and wherein said substitution is selected from the group consisting of halo, OR, and SR, wherein R is H or lower alkyl (1–4 C) and $AA_C$ is an amino acid coupled through a peptide bond to the remainder of the compound of Formula (1).

Determination of GST Complement

In general, two different approaches can be made to determine the GST complement of an "unknown" sample cell or tissue. First, as described above, using general techniques presently practiced in the art, the individual isoenzymes contained in the sample can be separated using affinity supports and tested individually for their patterns of activities. The individual isoenzymes from the sample can be obtained and then independently assessed for their substrate specificity, inhibitor specificity and for identifying substances which induce the activity or production of the isoenzyme.

In a second, less laborious, approach, pattern recognition techniques are employed to obtain an instant readout for samples of either or both unwanted and normal tissue for an individual subject by matching these patterns against a reference set prepared as above. In this approach, less volume of sample is required and no separation is necessary. This method is also useful when applied to tissue slices using histochemical staining for GST activity.

With respect to the first approach, a modification of the separation method used by Vos, R. M. E., et al., *Biochem Pharmacol* (1988) 37:1077–1082, can be used. In this method, the cytosol fraction from a complete rat liver was subjected to an affinity column of S-hexyl GSH Sepharose used as an affinity reagent for GSTs as a group. The eluted GST mixture was concentrated and separated by chromatofocusing on a mono-PHR 5/20 column (Pharmacia FPLC system). The individual isoenzymes were collected in separate fractions and analyzed. Fractions were identified by their position in the elution profile, their subunit molecular weight, and specific activities toward 1-chloro-2,4-dinitrobenzene, which is a substrate for most known GSTs.

By using as the affinity ligand a paralog chosen from among the compounds of the invention, milder conditions can be employed, and more active forms of the GST isoenzymes can be recovered. These are then tested for substrate specificity, etc.

As described above, one might consider the possibility of simply using arbitrary separation technology such as that of Vos that provides an elution pattern characteristic of the various GST isoenzymes, and matching the elution pattern for cells or tissue of unknown GST complement with the preset elution pattern to determine the nature of the GST complement in the unknown. One problem with this approach, however, lies in the genetic mutability of GST, so that it is difficult to make reliable matches that will retain the inferred characteristics and thus be assured to have similar reactivity patterns. The genetic mutability of the isoenzymes as well as their sensitivity to posttranslational modifications is very likely, in any particular case, to have a profound effect on the substrate specificity, inhibition patterns, and the like, as well as in binding and physical characteristics, such as pI. There is no guarantee that a correlation will exist between reactivity variation and physical property or binding variation; indeed, the probability is that the effects will not be correlated. As described above, this problem can be mitigated by using multiple affinity reagents, also provided by the invention compounds.

In the pattern-matching approach a more reliable assay is conducted by comparing the profile of reactivity of an unknown sample with a set of reference SC profiles. The application of this approach to the determination of the composition of analyte in general is described in copending application Ser. No. 07/678,049, filed 2 Apr. 1991, the disclosure of which is incorporated herein by reference. According to the techniques described in this application, a predetermined plot of profiles obtained from samples of known analyte composition is used as a reference with which an SC profile of the sample to be tested can be compared. Generally, a panel of 2–10, preferably 4–6, different specifically reactive reagents is first used to provide profiles for samples of known compositions. In the referenced application, specific binding assays were used where there was cross-reactivity by the candidate analytes across a panel of binding agents, and the profiles were obtained by measurement of inhibition values for binding of a known binding partner by various analytes. The collection of profiles is then treated mathematically by any of a number of techniques to generate a readable comparison with the corresponding SC profile of an unknown sample.

For use in determining the GST complements needed to practice the therapeutic methods of the invention, the analogous SC profiles can be determined using either isolated GST isoenzymes or mixtures thereof which contain known compositions or both. The specifically reactive reagents must include, as a panel, at least one, preferably three, and more preferably five GSH analogs of Formula 1, along with additional reagents, if desired. Such additional reagents may include a series of known substrates wherein turnover rates are measured. Suitable substrate candidates include, for example, ethacrynic acid, bromosulfophthalein, cumene hydroperoxide, BCNU, chlorambucil, trans-stilbene oxide and the like.

Also available for use as specifically reacting reagents which are members of the panel to provide a SC profile are inhibitors which interact with the GST isoenzyme at various levels. These inhibitors include, for example, piriprost, Cibacron Blue, and hematin. Antibodies which are specifically immunoreactive with the various isoenzymes can be used, as well as paralog-type affinity reagents. If the profile is to provide a basis for therapeutic strategy design, at least some members of the panel must be descriptive of the enzymatic activity of the GST.

An additional technique for obtaining SC profiles is analogous to that described by Takeo, K., et al., *J Immunol* (1978) 121:2305–2310. In this approach, differential electrophoresis in the presence of various binding agents for the individual proteins permits measurement of a mobility value. In the specific application described by Takeo, measurements of dextran-specific myeloma proteins in polyacrylamide gel electrophoresis were made, showing retardation when the dextrans were added to the separating gel, which retardation could be reversed by adding the hapten isomaltose oligosaccharide. In using this approach, a series of mobilities depending on the choice of retarding agent, for example, could be obtained for known compositions. This technique may be applied by using the novel compounds or panels of the invention as the retarding or mobilizing agents.

In one preferred method for determining the GST complement of biopsies, a series of HPLC columns is constructed using the known GgT substrates studied by Mannervik, B., et al., *Proc Natl Acad Sci* (1985) 82:7202–7206. These substrates are conjugated directly to the column supports or are attached to the GSH analog variants described by Adang, A. E. P., et al., *Biochem J* (1990) 269:47–54. A series of 50–100 different columns resulting from the various possible combinations of substrates with GSH analogs of Formula 1 represents a series of candidate sorbents. These sorbents are tested to select those of maximal diversity in properties by utilizing each for the separation of a mixture of known GST isoenzymes. The four or five colunms with the greatest differentiation capacities are then chosen as panel members for determining SC profiles in unknown samples and in standards.

Thus, rather than displaying the separations as elution patterns on each individual sorbent, the data are rearranged so that the capacity for adsorption to each sorbent represents an information channel in the SC profile of the isoenzyme. The reactivity pattern with respect to inducers, activators, substrates, and inhibitors are also determined for each isoenzyme and used as an information channel. The completed profile for each known isoenzyme is then used as a member of a reference set. Additional members of the reference sets are determined by utilizing samples from normal tissues and evaluating the values assigned to the same set of information channels. The corresponding profiles of biopsy samples from unknown, unwanted tissues are then compared against this reference set.

The profiles for known compositions are stored in computationally accessible form for comparison to profiles similarly determined for unknown samples. Thus, kits can be provided for determination of the GST complement of unknown samples which include the test panel members used in determination of the reference profiles along with instructions for SC profile determination of the unknowns. Suitable software to access the reference profiles may also be included. The GST complement can be used to characterize the sample tested and, if appropriate, may be used to design therapy.

For diseased tissue, the appropriate strategy can be selected for treatment. The complement may be evaluated to determine whether or not standard treatment protocols will be successful when applied to the unwanted cells or tissues or may be used for the design of different protocols including the choice of toxin or prodrug and the inclusion or noninclusion of a therapeutic modulator.

Synthesis of the Novel Tripeptide Analogs

The novel tripeptide analogs of the invention or additional tripeptide analog members of diverse panels can be synthesized using means generally known in the art, but using modifications which render these general methods applicable to the desired tripeptide. Although solid-phase synthesis methodologies can be used, liquid-phase peptide synthesis appears superior for these short peptides. The Fmoc reagents originally developed for solid-phase synthesis can be applied to a solution-phase method for producing 100 mg quantities of the tripeptide analogs.

The intermediate protected dipeptides and tripeptides synthesized using solution-phase Fmoc chemistry are isolated by chromatography on silica gel, and deprotected in mild base, thus allowing synthesis of acid-labile thioconjugates (Iselin, B., et al., *Helv Chem Acta* (1955) 38:1508–1516). The analogs can be purified and recovered, or the crude product mixtures may be directly coupled to solid support to provide affinity-derivatized supports (Sundburg, L., et al., *J Chromatog* (1974) 90:87–98).

In those circumstances where ester of the C-terminal amino acid $AA_C$ is not available, the ester is made by synthesizing the N-Fmoc-protected amino acid (Atherton, E., et al., in "Solid Phase Peptide Synthesis," IRL Press, Oxford, England (1989), pages 47–61) and then esterified by treatment with the desired alcohol in the presence of concentrated sulfuric acid (Benoiton, L., *Can J Chem* (1962) 40:570–572). Nonesterified materials are removed by extractions with mild base and the desired N-Fmoc amino acid ester is isolated by evaporation.

The sulfur-functionalized Fmoc cysteine derivatives are made in a one-pot procedure by treating cysteine with Fmoc-OSu as pH 9 and then treating this mixture with the appropriate alkylating agent.

The synthesis is conducted as shown in Reaction Scheme 1.

Reaction Scheme I

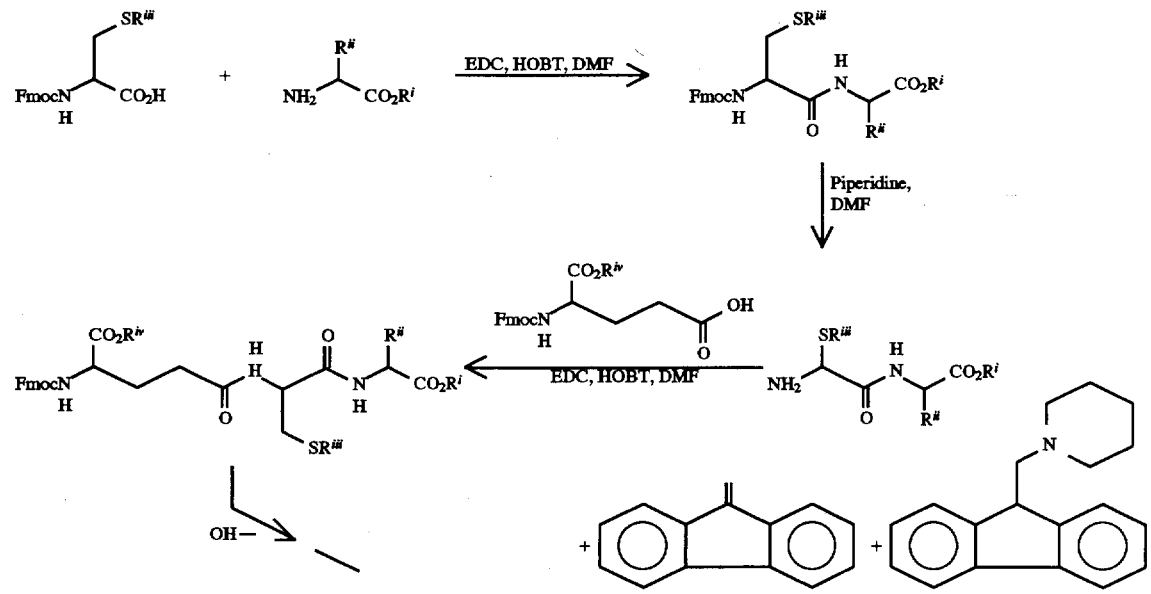

-continued
Reaction Scheme I

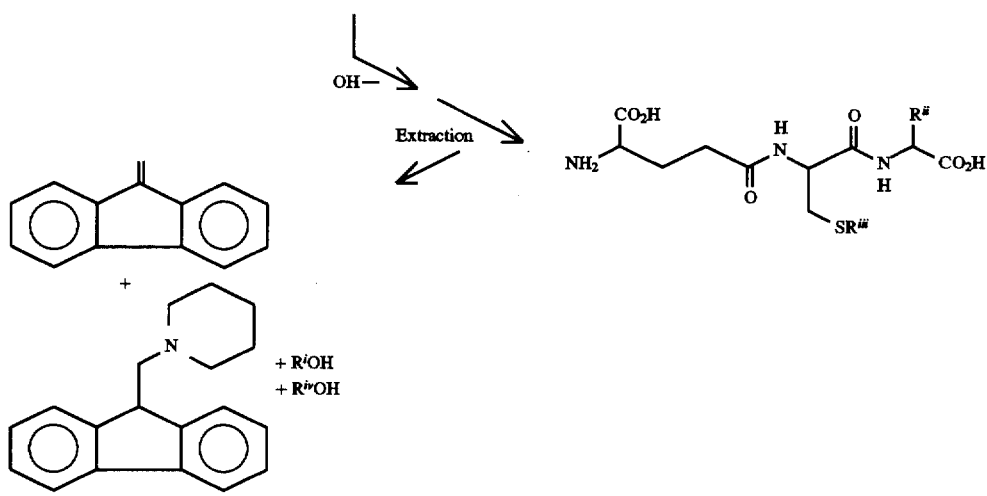

Coupling the cysteine derivative to the C-terminal amino acid is accomplished with the water-soluble carbodiimide EDC (Sheehan, J., et al., *J Org Chem* (1961) 26:2525–2528) and HOBT (Konig, W., et al., *Chem Ber* (1970) 103:788–798) (added to retard undesired racemization and speed up the reaction) in DMF. After coupling is complete, usually about 1 hr at r.t., the mixture is reduced in vacuo and poured into $KHCO_3$ solution (John Hughes, private communication). This step extracts most of the DMF and EDC and EDC urea, as well as some of the Fmoc-cysteine derivative which did not couple. The resulting gummy residue is retained by decanting off the liquid. This crude dipeptide is dissolved in EtOAc and washed with 1N hydrochloric acid and water to remove any remaining uncoupled C-terminal amino acid ester, as well as residual EDC and EDC urea. The solution is concentrated and the dipeptide purified by chromatography.

The recovered dipeptide is then treated with 25% piperidine in DMF for 30 min to remove the Fmoc group. The dibenzofulvene or its piperidine adduct resulting from Fmoc removal should not affect the results of the next coupling (Atherton, E., et al., *J Chem Soc Perkin Trans* (1981) 1:538–546). Any excess piperidine, however, must be removed, which is accomplished by repeated co-evaporation with DMF until the odor of piperidine is no longer detectable in the deblocked material. The second coupling is then performed with the glutamic acid derivative followed by the same workup as for the dipeptide.

Fmoc glutamic acid α-benzyl ester is made in good yield and purity from commercially available glutamic acid α-benzyl ester. Fmoc-glutamic acid α-tert butyl ester, also commercially available, can also be used, but this requires a separate acid treatment step in the workup. There are solubility problems with some of the protected tripeptides during this step, and impure, partially deprotected products are often obtained.

The material produced by the coupling of the glutamic acid derivative to the dipeptide and workup contains several chromatographically mobile components. The material that elutes first from the final column is fluorescent, suggesting dibenzofulvene. The putative desired product elutes next along with another UV-absorbing material, which is probably the piperidine adduct of dibenzofulvene. Since similar products are generated and separated from the deblocked tripeptide during the final workup, these contaminants are not removed at this stage.

Once the protected tripeptide (and impurities) are isolated, it is dried under vacuum and treated with 0.25N NaOH in 3:1 ethanol:water for 18 hrs. This removes the Fmoc and ester-protecting groups. When t-butyl-protected glutamic acid is used, 3N HCl in ethanol/water 3/1 v/v for 3 hr is used to remove the t-butyl group before the base treatment. The acid is removed by rotary evaporation and co-evaporation with ethanol and water, and the same base treatment as above removes the remaining protecting groups. After the overnight base treatment, addition of water and extraction with hexane removes the organic by-products of the deprotection. The aqueous solution of the peptide is acidified and reduced to a solid. Dissolution of the peptide in ethanol and filtration removes the salt. This is evaporated to a foam and subjected to high vacuum overnight.

The compounds are analyzed by HPLC, TLC and FAB mass spectroscopy. While the TLC analysis show good results in most cases, the HPLC results are mixed, partially because the analysis conditions used were not optimized for some of the more hydrophobic (S-alkyl C-terminal valine, b-alanine and 4-ABU) peptides.

Racemization during the final deprotection with base may occur in some small amount, particularly with the phenylglycine analog (Bodansky, M., et al., in "Practical Methods in Peptide Synthesis," Springer Verlag, Berlin (1984)). This is less than that which occurs with the sodium-ammonia conditions used previously by Adang, A. et al. (*Biochem J* (1989) 264:721–724).

Using the techniques set forth above, the analogs of Table 1 were prepared.

TABLE 1

| Compound[a] | Yield, %[b] | TLC Rf[c] | M/e[d] | Loading[e] |
|---|---|---|---|---|
| gE-C(Bz)-G | 32 | 0.49 | 388.2, 402.2[f] | 1.0 |
| gE-C(Pr)-A | 23 | 0.71 | 365.2 | 9.0 |
| gE-C(Hx)-A | 17 | 0.76 | 406.2, 428.2[f] | 4.8 |
| gE-C(Bz)-A | 44 | 0.35 | 412.2, 434.2[f] | 6.6 |
| gE-C(Trt)-A | 15 | 0.83 | 586.4[f] | 1.2 |
| gE-C(Me)-bA | 27 | 0.58 | 357.1[f] | |
| gE-C(Pr)-bA | 27 | 0.41 | 364.1, 386.1[f] | |

TABLE 1-continued

| Compound[a] | Yield, %[b] | TLC Rf[c] | M/e[d] | Loading[e] |
|---|---|---|---|---|
| gE-C(Hx)-bA | 13 | 0.49 | 406.3, 428.3[f] | 6.0 |
| gE-C(Bz)-bA | 17 | 0.66 | 434.2[f] | 8.1 |
| gE-C(Trt)-bA | 42 | 0.92 | 564.3, 586.5[f] | N/A |
| gE-C(Pr)-4ABu | 13 | 0.51 | 378, 400[f] | |
| gE-C(Hx)-4ABu | 17 | 0.52 | 402.3, 424.3[g] | 4.6 |
| gE-C(Bz)-4ABu | 23 | 0.70 | 426, 448.2[f] | 4.0 |
| gE-C(Pr)-V | 23 | 0.67 | 391 | 13.7 |
| gE-C(Hx)-V | 15 | 0.64 | 434.2, 456.2[f] | 19.5 |
| qE-C(Bz)-V | 26 | 0.73 | 440.1, 462.1[f] | 6.5 |
| gE-C(Pr)-D | 33 | 0.55 | 408 | 7.0 |
| gE-C(Hx)-D | 25 | 0.68 | 451.2 | 5.9 |
| gE-C(Bz)-D | 22 | 0.59 | 456.1, 478.1[f] | 2.4 |
| gE-C(Pr)-PG | 14 | 0.64 | 426.4, 448[f] | |
| gE-C(Hx)-PG | 13 | 0.63 | 468.3 | 4.8 |
| gE-C(Bz)-PG | 11 | 0.61 | 474.1, 496.1[f] | 2.0 |
| gE-C(Pr)-H | 6 | 0.57 | 429.2 | |
| gE-C(Hx)-H | 30 | 0.61 | 473.3 | 6.0 |
| gE-C(Bz)-H | 11 | 0.58 | 499.3[f] | 1.0 |

[a]Standard 20-letter AA code, with Me = methyl, Pr = n-propyl, Hx = n-hexyl, Bz = benzyl, Trt = trityl (triphenyl methyl).
[b]Moles of deprotected product divided by the moles of Fmoc-cysteine derivative used.
[c]TLC $R_f$ values for silica plates eluted with EtOAc/pyridine/HOAc/water 5/5/3/1 and visualized with ninhydrin spray.
[d]Observed molecular mass, in AMU, usually the molecular weight plus 1. Thioglycerol or nitrobenzyl alcohol matrix.
[e]Micromoles of peptide per mL of swollen resin volume (water)
[f]Sodium adduct, M + 22.
[g]Molecular ion and sodium adduct minus water; MH+ − 18.

The following examples are intended to illustrate, but not to limit, the invention.

EXAMPLE 1

Synthesis of 9-Fluorenylmethoxycarbonyl-4-aminobutyric acid ethyl ester

Forty-five g (0.1339M, 0.94 eq) of Fmoc-Osu was added slowly to a solution of 14.75 g (0.143M, 1 eq) of 4-aminobutyric acid (4-ABu) and 20 g of $Na_2CO_3$ in 300 mL of deionized water and 200 mL of tetrahydrofuran (THF). The pH was monitored and more $Na_2CO_3$ was added to keep the pH above 8. The reaction was stirred for 2 hr and then acidified with conc. HCl. The resulting cloudy suspension was extracted with 600 mL of ethyl acetate (EtOAc), after which the organic layer was further extracted with 300 mL 0.5N NaOH. The aqueous layer was rapidly poured into 20 mL of conc. HCl in 500 mL of ice water. The resulting white suspension was extracted with 300 mL of EtOAc, dried over 50 g of $Na_2SO_4$ and evaporated to 35 g (76% yield) of Fmoc-4-ABu as a white powder. This was dissolved in 500 mL of absolute ethanol and 40 mL of conc. $H_2SO_4$ was added. After 4 hrs, the solution had become a semi-solid white mass. This was poured into 2 L of water and filtered. The white material was dissolved in 500 mL of EtOAc and extracted once with 200 mL of 0.5N NaOH, dried and evaporated to give 30 g (79% yield) of total compound, $R_f$ 0.71 (20% MeOH in $CH_2Cl_2$), mp 83°–86°.

Anal. Calcd. for $C_{21}H_{23}NO_4$: C, 71.37; H, 6.56; N, 3.96. Found: C, 71.42; H, 6.67; N, 3.72.

EXAMPLE 2

Synthesis of 9-flourenylmethoxycarbonyl-phenylglycine ethyl ester

In a similar synthetic procedure, 20 g of phenylglycine gave 33.7 g (68% yield) of Fmoc-phenylglycine. 19 g of this product was converted into 10 g (57% yield) of product, $R_f$ 0.95 (same TLC system), mp 130°–133°.

Anal. calcd. for $C_{25}H_{23}NO_4$: C, 74.80. H, 5.77. N, 3.49. Found: C, 74.72, H, 5.91, N, 3.20.

EXAMPLE 3

Synthesis of 9-flourenylmethoxycarbonyl-aspartic acid dimethyl ester

Forty-five g (0.134M, 0.96 eq) of Fmoc-Osu was added to 20 g (0.15M, 1 eq) of aspartic acid and 20 g of $Na_2CO_3$ dissolved in 400 mL of water and 200 mL of dioxane. The mixture was stirred for 2 hrs while the pH was maintained at about 9 by the addition of small amounts of $Na_2CO_3$. Then the cloudy white mixture was poured into 500 mL of ice water containing 40 mL of conc HCl. The white solid was extracted with 500 mL EtOAc and this was mixed with 500 mL of hexane. The mixture was chilled overnight and stirred the next day to give 38 g of Fmoc-aspartic acid as crystals (71% yield) upon filtration and air drying. 10 g (0.28M) of this product was dissolved in 200 mL of methanol and 20 mL of conc $H_2SO_4$ was added. The solution was allowed to stand overnight. The mixture was poured into 1 L of water and filtered. The resulting white solid was dried and redissolved in EtOAc. Slow addition of hexane and chilling gave 9 g (83% yield) of product as white needles, mp 78°–80°. $[a]_d = -13.9°$.

Anal. calcd. for $C_{21}H_{21}NO_4$: C, 65.78. H, 5.52. N, 3.65. Found: C, 66.18. H, 5.68. N, 3.69.

EXAMPLE 4

Synthesis of 9-flourenylmethoxycarbonyl-S-hexyl cysteine

A. Twenty g (0.127M, 1 eq) of cysteine hydrochloride and 20 g $Na_2CO_3$ was dissolved in 800 ml of water under a stream of argon. Two hundred mL of $CH_3CN$ was added, and then 42 g (0.122M, 0.96 eq) of Fmoc-Osu was added in small portions while the pH was maintained at about 9 by adding 5 g portions of $Na_2CO_3$. The reaction was stirred for an additional 2 hrs, and 18.6 mL (26.8 g, 0.126M, 0.99 eq) of 1-iodohexane was added as a solution in 200 mL of $CH_3CN$. The reaction was stirred for an additional 2 hrs and poured into 1 L of ice water and 50 mL of conc HCl. The white mixture was extracted with 600 mL of EtOAc, and the organic layer was extracted with 2 500 mL portions of 1N KOH. Each of these was immediately dropped into separate portions of 500 ml of water and 30 mL of conc HCL, and the cloudy mixtures obtained were each extracted with 500 ml of EtOAc. These were each dried over $Na_2SO_4$ and evaporated. The total yield was 24.6 g (45%). The second fraction (3.5 g) crystallized on standing, mp 101°–103°. $R_f$=0.57. $[a]_d = -14.3°$.

Anal. Calcd. for $C_{21}H_{23}NO_4S$: C, 65.42. H, 6.01. N, 3.63. Found: C, 65.53. H, 5.74. N, 2.91.

B. Additional S-functionalized Fmoc cysteine derivatives were prepared as set forth in paragraph A.

EXAMPLE 5

Synthesis of Fmoc-glutamic acid α-benzyl ester

Twenty-five g (0.105M) glutamic acid α-benzyl ester and 25 g $Na_2CO_4$ was dissolved in 400 mL of water and 200 mL THF was added. 34 g (0.101M, 0.96 eq) Fmoc-OSu was added in small portions with stirring, and the pH was kept at about 9 by adding more $Na_2CO_3$ as needed. After 1 hr, the reaction was poured into 500 mL of water and acidified with conc HCl. The white suspension was extracted with EtOAc, dried over $Na_2SO_4$ and evaporated to a solid mass. This was dissolved in 500 mL hot EtOAc and 300 mL hexane was added. Overnight chilling, collection and air-drying gave 38.7 g (83% yield) of white crystals, mp 110°–112°. $[a]_d=$ –13.8°. M/e (Rel. inten.): 460.2 (19), 363.4 (8), 345.4 (19), 307.2 (10), 289.2 (12), 238.2 (12), 191.2 (10), 178.2 (89), 165.1 (23), 154.1 (57), 136.1 (48). $^1H$ NMR (400 mHz), PPM: 1.9 (m, 1H), 2.2 (m, 1H), 2.4 (M, 2H), 4.1 (t, 1H), 4.4 (d, 2H), 4.43 (m, 1H), 5.1 (s, 2H), 5.6 (d, 1H), 7.3 (m, 9H), 7.5 (d, 2H), 7.7 (d, 2H), 9.4–9.6 (broad s, 1H). $^{13}C$ (100 mHz), PPM: 27.5, 30.0, 47.3, 53.5, 67.3, 67.7, 120.2, 125.0, 127.3, 128.5, 128.8, 129.2, 135.2, 141.5, 143.6, 143.9, 156.3, 171.4, 177.8.

Anal. Calcd. for $C_{27}H_{25}NO_6$: C, 70.57. H, 5.48. N, 3.05. Found: C, 69.71. H, 5.58. N, 2.88.

EXAMPLE 6

Synthesis of γ-glutamyl S-benzyl cysteinyl β-alanine 1.5 g (9.76 mmol, 1 eq) of β-alanine ethyl ester hydrochloride was added to 50 mL of DMF and 1.8 mL of DIPEA was added. 3.5 g (8.1 mM, 0.83 eq) of Fmoc-S-benzyl cysteine was added and dissolved by swirling the solution. Next 2 g of EDAC and 250 mg of HOBT were added, and the solids were dissolved by swirling. The mixture was allowed to stand for 1 hr, and was concentrated in vacuo to a mobile oil of about 5 mL in volume. To this was added 100 mL of 10% weight/volume $KHCO_3$ in water, and the mixture was shaken and the liquid removed by filtration. The residue was dissolved in 100 mL of EtOAc, washed with 50 mL of 1N HCl, 50 mL of water and dried over $Na_2SO_4$. The solution was filtered and concentrated in vacuo to give a foam which was chromatographed using a 2×6 cm bed of silica gel packed in $CH_2Cl_2$. The column was eluted until the first UV absorbing material appeared, then a gradient was run in 1% methanol increments of 100 mL volume to 3% methanol. A strong UV absorbing band eluted after two portions of 3% methanol; these were checked for purity by TLC and pooled and evaporated in vacuo to give 4.6 g (83% yield) of Fmoc-Cys(S-benzyl)-betaalanine ethyl ester. Half of this (4 mmol) was dissolved in a mixture of 30 mL DMF and 10 mL piperidine, and allowed to stand for 30 min. The solution was reduced to a solid in vacuo, and the process was repeated twice again with 50 mL of DMF. The resulting white solid was subjected to a high vacuum for 1 hr, then it was dissolved in 50 mL of DMF. For the second coupling step, 1.6 g (3.5 mmol, 0.9 eq) of Fmoc-glutamic acid (α) benzyl ester (v) was added, followed by 0.8 g (4.2 mmol, 1.05 eq) of EDAC and 200 mg (1.4 mmol) of HOBT. The mixture was allowed to stand 1 hr, and concentrated in vacuo to about 5 mL in volume. This was poured into 100 mL of 10% aqueous $KHCO_3$ solution and shaken. The liquid was poured off, and the residue was dissolved in 100 mL of ethyl acetate. The organic layer was washed with 50 mL of 1N HCl, 50 mL of water, and dried over $Na_2SO_4$. This was reduced to a tar and chromatographed in the same manner as the protected dipeptide. 1.2 g (42% yield) of the protected tripeptide was obtained. This material was dissolved in 30 mL of absolute ethanol and 10 mL of 1N NaOH solution was added. The mixture was allowed to stand for 18 hrs, and was poured into a separatory funnel with 40 mL of water and 40 mL of hexane. The layers were shaken and separated, and the aqueous phase was washed with an additional 40 mL of hexane. The pH of the water layer was adjusted to about 3 by adding a few drops of conc HCl, and the cloudy solution was reduced to a solid in vacuo and subjected to a high vacuum for several hrs. The residue was washed with 2 20 mL portions of absolute ethanol. The ethanol-NaCl slurry was filtered, and the clear solution was evaporated to a tar. The weight was 620 mg (89% yield from the protected tripeptide, 19% from Fmoc-Cys(Benzyl)-OH). A TLC plate was run in ethyl acetate/pyridine/water/acetic acid 5/5/3/1 v/v and visualized with ninhydrin spray and heat (Stewart, J. et al., "Solid Phase Peptide Synthesis" (1984) pp. 53–124, Pierce Chemical Co., Rockford, Ill., $R_f0.66$. HPLC analysis showed 74% purity by area integration of UV absorbing material (FIG. 1). Fast atom bombardment Mass spectroscopy (FABMS) showed an ion peak at 434.2 M/e, consistent with the tripeptide monosodium salt. Other higher mass peaks were also present, attributable in part to incompletely deprotected peptide.

In cases where the Fmoc protected C-terminal amino acid ester was used instead of the commercially available free amino C-terminal amino acid ester, this material was deblocked with the same procedures as those used to deblock the protected dipeptide above, then proceeding with the first coupling reaction as above.

EXAMPLE 7

Derivatization to Sepharose Resin 0.66 g epoxy Sepharose™ 6B (Pharmacia) was swollen with 10 mL water for 15 min, then rinsed twice with 10 mL water in a 15 mL sintered glass funnel. A solution of 100–500 mg of the crude tripeptide in 5 mL ethanol and 10 mL water was adjusted to pH 11–12 with 6N NaOH in a 20 mL scintillation vial with a polycone cap. The rinsed resin was added, and gently agitated overnight in a 37° water bath. The pH was checked the next day and brought back to pH 11–12 with 6N NaOH if needed. After another day of agitation, the resin was filtered (the peptide-containing liquid was acidified with conc HCl, evaporated and saved) and rinsed three times with 10 mL water. The unfunctionalized epoxy groups were capped by soaking the resin in 10 mL of water which contained about 0.1 mL ethanolamine for 1 hr. The resin was then rinsed three times with 10 mL water, and a sample was removed for analysis. The remainder was rinsed with 10 mL of 0.1M NaOAc, 0.5M NaCl pH 4.0 buffer, followed by 10 mL of 0.1M tris chloride, 0.5M NaCl pH 8.0 buffer. The resin was stored at 4° C. in this pH 8 buffer.

EXAMPLE 8

Use of the Compounds of the Invention as Affinity Sorbents

A series of the compounds of Formula 1 was constructed wherein YCO was γ-Glu, $AA_C$ was Gly, and X was benzyl having at the para position, nitro, chloro, methoxy and methyl substituents. The relevant analogs were derivatized to Sepharose resin as described above and used as affinity sorbents in the separation of three recombinant human GST enzymes. HPLC was used to measure the relative amounts of the enzymes which bound to the supports.

The results are shown in Table 2.

TABLE 2

| Substituent | %π | %μ |
|---|---|---|
| NO$_2$ | 95 | 5 |
| Cl | 89 | 11 |
| Ome | 70 | 17 |
| Me | 3 | 94 |

When the percentage of π and μ isoenzymes were plotted against their sigma (meta) values good linear correlation was obtained. However, poor correlation was obtained when the sigma (para) values were used. The sigma (meta) values are a measure of purely inductive effect; however, the sigma (para) values are dependent on resonance in which the substituent can place partial charges at an atom in the ring next to the point of attachment.

We claim:

1. A compound of the formula:

(1)

or a salt thereof;

wherein n is 1 or 2;

wherein when n is 1, X is a mono- or disubstituted or unsubstituted $C_{1-20}$ hydrocarbon radical wherein any substitution is selected from the group consisting of halo, OR, and SR, wherein R is H or $C_{1-4}$ alkyl;

and wherein, when n is 2, one X is defined as for n=1 and the other X is lower $C_{1-4}$ alkyl;

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3..4
        ( D ) OTHER INFORMATION: /note= "This position is
          ( B z )(Et)-."

( i x ) FEATURE:
        ( A ) NAME/KEY: Modified-site
        ( B ) LOCATION: 4
        ( D ) OTHER INFORMATION: /note= "This position is 4ABu."

( x i ) SEQUENCE DESCRIPTION: SEQ ID NO:1:

Glu  Gly  Cys  Xaa
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3..4
        ( D ) OTHER INFORMATION: /note= "This position is (Hx)-."

( x i ) SEQUENCE DESCRIPTION: SEQ ID NO:2:

Asp  Gly  Cys  Phe
    1

Y is 
$$\begin{array}{c} \text{H}_2\text{NCH(CH}_2)_m - ; \\ | \\ \text{COOH} \end{array}$$

wherein m is 1 or 2;

AA$_C$ is an amino acid coupled through a peptide bond to the remainder of the compound of Formula (1) selected from the group consisting of glycine, valine, alanine, 4-aminobutyric acid, aspartic acid, phenylglycine, histidine, tryptophan, tyrosine, and phenylalanine, wherein the phenyl group of phenylalanine or phenylglycine may optionally contain a single substitution selected from the group consisting of halo, OR, and SR, wherein R is H or C$_{1-4}$ alkyl;

with the proviso that if Y is $$\begin{array}{c} \text{H}_2\text{NCHCH}_2\text{CH}_2 - , \\ | \\ \text{COOH} \end{array}$$

AA$_C$ is not Gly;

and if Y is $$\begin{array}{c} \text{H}_2\text{NCHCH}_2\text{CH}_2 - , \\ | \\ \text{COOH} \end{array}$$

and X is benzyl, AA$_C$ cannot be Val.

2. The compound of claim 1 wherein when n=1, X is an unsubstituted hydrocarbon radical and wherein when n=2, one X is an unsubstituted hydrocarbon radical and the other X is C$_{1-4}$ alkyl.

3. The compound of claim 2 wherein said hydrocarbon radical is C$_{1-6}$ alkyl or comprises or substituted aromatic group.

4. The compound of claim 3 wherein said hydrocarbon radical is methyl, propyl, hexyl, benzyl, or trityl.

5. The compound of claim 3 wherein n is 1 and Y is $$\begin{array}{c} \text{Y is H}_2\text{NCH(CH}_2)_m - ; \\ | \\ \text{COOH} \end{array}$$

and wherein m=2.

6. The compound of claim 5 wherein the hydrocarbon radical is methyl, propyl, hexyl, benzyl or trityl.

7. The compound of claim 6 wherein AA$_C$ is valine.

8. The compound of claim 6 wherein AA$_C$ is aspartic acid.

9. The compound of claim 6 wherein AA$_C$ is phenylglycine.

10. The compound of claim 6 which is selected from the group consisting of gE-C(Pr)-A; gE-C(Hx)-A; gE-C(Bz)-A; gE-C(Trt)-A; gE-C(Pr)-4ABu; gE-C(Hx)-4ABu; gE-C(Pr)-V; gE-C(Hx)-V; gE-C(Pr)-D; gE-C(Hx)-D; gE-C(Bz)-D; gE-C(Pr)-PG; gE-C(Hx)-PG; gE-C(Bz)-PG; gE-C(Pr)-H; gE-C(Hx)-H; gE-C(Bz)-H and salts thereof.

11. The compound of claim 10 which is selected from the group consisting of gE-C(Pr)-PG; gE-C(Hx)-PG; gE-C(Bz)-PG and their salts.

12. The compound of claim 11 which is gE-C(Bz)-PG or its salts.

13. A panel comprising at least five diverse tripeptide glutathione analogs, wherein each of said analogs is a compound of the formula:

$$\begin{array}{c} \text{Y} - \text{CO} - \text{NHCHCO} - \text{AA}_c \\ | \\ \text{CH}_2 - \text{S} - (\text{X})_n \end{array} \quad (1)$$

or C$_{1-6}$ monoalkyl amides, C$_{1-6}$ alkyl esters, salts or cycloamido forms thereof;

wherein n is 1 or 2;

wherein when n is 1, X is H, a mono- or disubstituted or unsubstituted C$_{1-20}$ hydrocarbyl moiety optionally containing 1 or 2 nonadjacent heteroatoms selected from the group consisting of O, S and N, and wherein any substitution is selected from the group consisting of halo, OR, and SR, wherein R is H or C$_{1-4}$ alkyl;

and wherein, when n is 2, one X is lower C$_{1-4}$ alkyl, and the other X is as above defined for n=1 except neither X=H;

Y is 
$$\begin{array}{c} \text{H}_2\text{NCH(CH}_2)_m - ; \\ | \\ \text{COOH} \end{array}$$

$$\begin{array}{c} \text{HOOC(CH}_2)_m\text{CH} - ; \\ | \\ \text{NH}_2 \end{array}$$

$$\begin{array}{c} \text{H}_2\text{NCH(CH}_2)_m\text{CO} - \text{NHCH}_2 - ; \text{ or} \\ | \\ \text{COOH} \end{array}$$

$$\begin{array}{c} \text{HOOC(CH}_2)_m\text{CHCO} - \text{NHCH}_2 - \\ | \\ \text{NH}_2 \end{array}$$

wherein m is 1 or 2; and

AA$_C$ is an amino acid coupled through a peptide bond to the remainder of the compound of Formula (1) selected from the group consisting of glycine, valine, alanine, β-alanine, 4-aminobutyric acid, aspartic acid, phenylglycine, histidine, tryptophan, tyrosine, and phenylalanine, wherein the phenyl group of phenylalanine or phenylglycine may optionally contain a single substitution selected from the group consisting of halo, OR and SR, wherein R is H or C$_{1-4}$ alkyl;

wherein said compounds have systematically varied values of at least one property that determines the ability of the compound to bind to an enzyme which binds glutathione and wherein at least one member of the panel is a compound of claim 1.

14. The panel of claim 13 wherein said property is selected from the group consisting of hydrophobicity of X, charge of X, Hammett's Constants of X, charge of AA$_C$, Hammett's Constants of AA$_C$ and hydrophobicity of AA$_C$.

15. A compound of the formula $$\begin{array}{c} \text{Y} - \text{CO} - \text{NHCHCO} - \text{AA}_c \\ | \\ \text{CH}_2 - \text{S} - (\text{X})_n \end{array} \quad (1)$$

or a salt thereof;

wherein n is 1 or 2;

wherein when n is 1, X is a mono- or disubstituted or unsubstituted C$_{3-20}$ hydrocarbon radical containing no heteroatoms in any radical wherein said substitution is selected from the group consisting of halo and OR wherein R is H or C$_{1-4}$ alkyl;

and wherein, when n is 2, one X is defined as for n=1 and the other X is lower C$_{1-4}$ alkyl;

Y is H$_2$NCH(CH$_2$)$_m$—;
|
COOH wherein m is 1 or 2; and

AA$_C$ is β-alanine.

16. The compound of claim 15 wherein when n=1, X is an unsubstituted hydrocarbon radical and wherein when n=2, one X is an unsubstituted hydrocarbon radical and the other X is C$_{1-4}$ alkyl.

17. The compound of claim 15 wherein n is 1 and Y is

H$_2$NCH(CH$_2$)$_m$—;
|
COOH and wherein m=2.

18. The compound of claim 15 which is gE-C(Pr)-bA; gE-C(Hx)-bA; gE-C(Bz)-bA; gE-C(Trt)-bA; or their salts.

* * * * *